United States Patent [19]
Muschler

[11] Patent Number: 6,049,026
[45] Date of Patent: *Apr. 11, 2000

[54] APPARATUS AND METHODS FOR PREPARING AN IMPLANTABLE GRAFT

[75] Inventor: George Frederick Muschler, Cleveland Heights, Ohio

[73] Assignee: The Cleveland Clinic Foundation, Cleveland, Ohio

[ * ] Notice: This patent is subject to a terminal disclaimer.

[21] Appl. No.: 09/082,984

[22] Filed: May 21, 1998

Related U.S. Application Data

[63] Continuation-in-part of application No. 08/675,498, Jul. 3, 1996, Pat. No. 5,824,084.

[51] Int. Cl.[7] .............................. A61F 2/28; A61K 39/40; B01D 15/08
[52] U.S. Cl. ........................ 623/16; 424/164.1; 210/659
[58] Field of Search .......................... 623/16; 424/164.1; 210/659

[56] References Cited

U.S. PATENT DOCUMENTS

| | | |
|---|---|---|
| 4,608,199 | 8/1986 | Caplan et al. . |
| 4,609,551 | 9/1986 | Caplan et al. . |
| 5,197,985 | 3/1993 | Caplan et al. . |
| 5,226,914 | 7/1993 | Caplan et al. . |
| 5,486,359 | 1/1996 | Caplan et al. . |
| 5,645,729 | 7/1997 | Priegnitz et al. ........................ 210/659 |
| 5,700,289 | 12/1997 | Breibart et al. ............................ 623/16 |
| 5,718,899 | 2/1998 | Gristina et al. ....................... 424/164.1 |
| 5,824,084 | 10/1998 | Muschler ................................... 623/16 |

OTHER PUBLICATIONS

John M. Clark, Jr and Robert L. Switzer, Experimental Biochemistry, pp. 16 and 243, 1964.

Primary Examiner—Michael J. Milano
Assistant Examiner—Hieu Phan
Attorney, Agent, or Firm—Calfee, Halter & Griswold LLP

[57] ABSTRACT

A kit for preparing an implantable graft, particularly an implantable, composite bone graft is provided. The kit includes a porous, biocompatible, sterile substrate and a container configured to retain the substrate and to permit flow of a cell suspension, particularly a bone marrow aspirate suspension therethrough. A method which employs such kit for preparing a composite implantable bone graft is also provided. The method includes the steps of providing a bone marrow aspirate suspension and passing the bone marrow aspirate suspension through a porous, biocompatible, implantable substrate to provide a composite bone graft having an enriched population of connective tissue progenitor cells. The composite bone graft prepared by the present method contains an enriched population of connective tissue progenitor cells and a greater number of connective tissue progenitor cells per unit volume than that found in the original bone marrow aspirate. The present invention also relates to a composite bone marrow graft prepared according to the present method.

20 Claims, 5 Drawing Sheets

APPARATUS AND METHODS FOR PREPARING AN IMPLANTABLE GRAFT

CROSS-REFERENCE TO RELATED APPLICATIONS

This application is a continuation-in-part of the commonly assigned, U.S. patent application Ser. No. 08/675,498, filed Jun. 3, 1996, which issued on Oct. 20, 1998, as U.S. Pat. No. 5,824,084.

The present invention was made with support from National Institutes of Health Grant NO. AR42997-01. The United States Government has certain rights in the invention.

BACKGROUND OF THE INVENTION

Bone grafting is widely used to treat fractures, non-unions and to induce arthrodeses. Autogenous cancellous bone, which is taken from one site in the graftee and implanted in another site in the graftee, is currently the most effective bone graft. Autogenous cancellous bone provides the scaffolding to support the distribution of the bone healing response. Autogenous cancellous bone also provides the connective tissue progenitor cells which form new cartilage or bone. However, the harvest of autogenous bone results in significant cost and morbidity, including scars, blood loss, pain, prolonged operative and rehabilitation time and risk of infection. Furthermore, in some clinical settings, the volume of the graft site can exceed the volume of the available autograft. Accordingly, alternatives to autografts have been developed in an attempt to reduce the morbidity and cost of bone grafting procedures.

Several purified or synthetic materials, including ceramics, biopolymers, processed allograft bone and collagen-based matrices have been investigated or developed to serve as substitutes for autografts. The FDA has approved a porous coral derived synthetic hydroxyapatite ceramic for use in contained bone defects. A purified collagen/ceramic composite material is also approved for use in acute long bone fractures. Although these materials avoid the morbidity involved in harvesting autografts from the graftee and eliminate problems associated with a limited amount of available autograft, the clinical effectiveness of the synthetic materials remains generally inferior to autografts.

The synthetic graft materials have also been used as carriers for bone marrow cells. When such composite materials have been implanted into skeletal defects, the connective tissue progenitor cells differentiated into skeletal tissue. In some instances, the composite implants were made by soaking the synthetic graft material in a cell suspension obtained from a bone marrow plug. However, the connective tissue progenitor cells, which have the capacity to differentiate into cartilage, bone and other connective tissue such as fat, muscle, and fibrous tissue are present in the bone marrow in very minute amounts. The numbers of such cells present in 1 ml of bone marrow varies widely from subject to subject from about 100 cells to 20,000 cells. This represents a mean of about one in 20,000 to one in 40,000 of the nucleated cells in bone marrow. Thus, a composite implant made by soaking a given volume of synthetic carrier graft material in a comparable volume of fresh bone marrow contains relatively few connective tissue progenitor cells.

Accordingly, a technique has been previously developed to increase the relative concentration of connective tissue progenitor cells in composite implants. This technique involves plating a suspension of bone marrow cells onto tissue culture dishes, culturing the cells in a select medium for one or more days until the number of connective tissue progenitor cells in the culture increases, and then detaching the cells from the tissue culture dishes to provide a cell suspension containing a culturally-expanded population of connective tissue progenitor cells. Composite implants are then made by soaking synthetic ceramic carriers in this suspension of culturally-expanded cells. Unfortunately, this method of preparing composite implants is very time consuming. Moreover, if the culturally-expanded cells used in this method are derived from bone marrow aspirates obtained from the graftee, the graftee must undergo multiple invasive procedures, one to remove his or her bone marrow and one at a later date to implant the composite implant. In addition, the graftee may be exposed to anaesthesia more than once.

Accordingly it is desirable to have a new method of preparing a composite bone marrow graft which can be performed intraoperatively, i.e., at the same time bone marrow is being taken from the graftee. An intraoperative method of preparing a composite bone marrow graft which uses bone marrow aspirate as the source of the connective tissue progenitor cells and which results in the formation of a composite bone graft containing an enriched population of connective tissue progenitor cells is especially desirable.

SUMMARY OF THE INVENTION

The present invention provides a new and improved method for preparing an implantable graft, particularly a composite bone graft. As used hereinafter the term "bone graft" refers to a graft which comprises connective tissue progenitor cells and is, therefore, capable of differentiating into cartilage or bone. The method comprises providing a bone marrow aspirate suspension and passing the bone marrow aspirate suspension through a porous, biocompatible, implantable substrate to provide a composite bone graft having an enriched population of connective tissue progenitor cells. Because the method is preferably performed intraoperatively using a bone marrow aspirate from the graftee, it reduces the time and expense required for graft preparation and also the number of times the graftee must return to the operating room to undergo invasive procedures. The improved composite bone graft prepared by the present method contains an enriched population of connective tissue progenitor cells and a greater number of connective tissue progenitor cells per unit volume than that found in the original bone marrow aspirate.

The present invention also relates to a composite bone marrow graft prepared according to the present method.

The present invention also provides a kit comprising the apparatus for preparing an implantable graft, particularly a composite bone graft. The kit comprises a porous, biocompatible substrate and a container configured to retain said substrate and to permit flow of a cell suspension, particularly a bone marrow aspirate suspension therethrough. Preferably, the substrate is sterile.

DETAILED DESCRIPTION OF THE INVENTION

Figure 1:
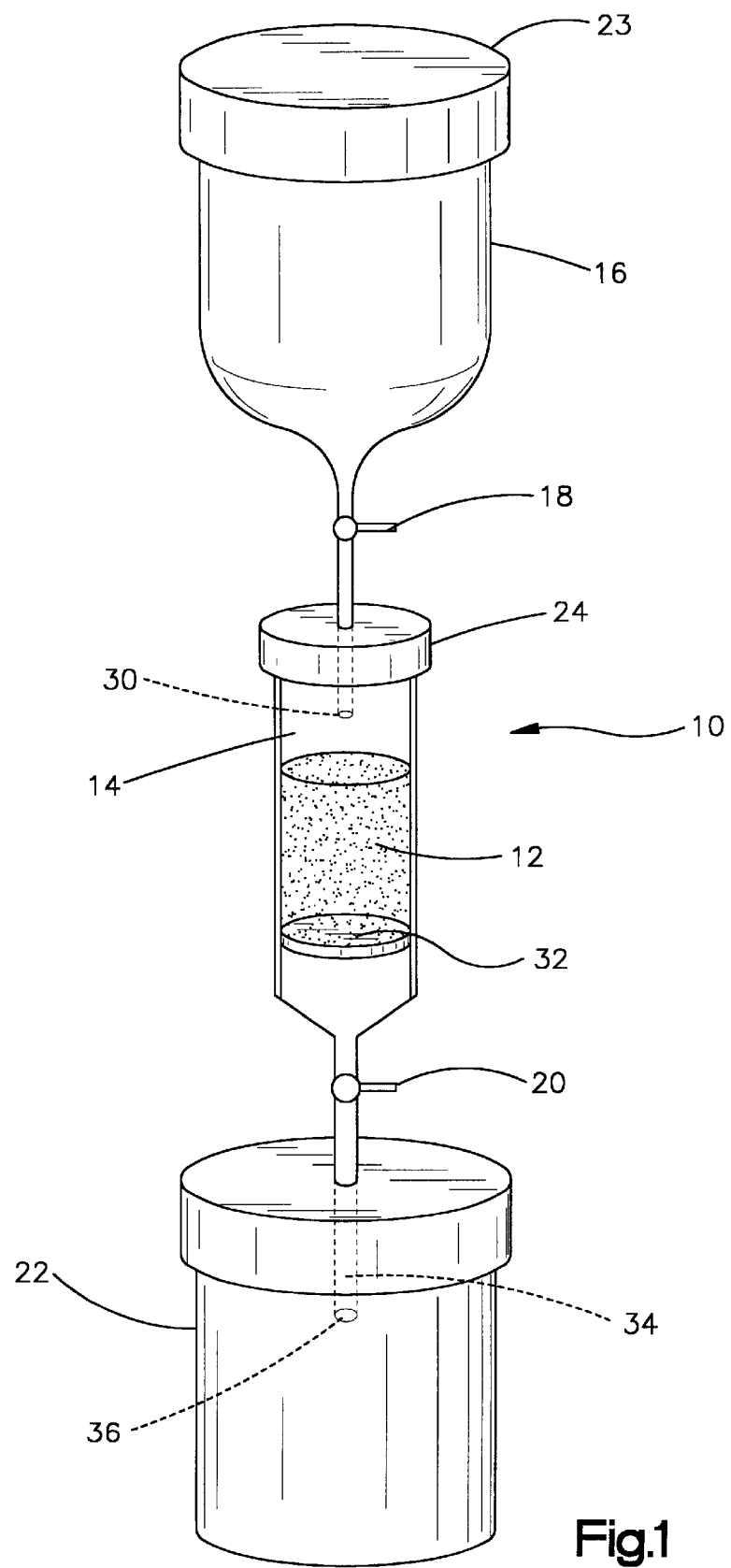
FIG. 1 is a representation, somewhat schematic, of an apparatus used to prepare a composite bone graft in accordance with the present invention.

The present invention provides a new and improved method for preparing a composite bone graft. The method comprises collecting a bone marrow aspirate from a donor, preferably in the presence of an anti-coagulant to provide a bone marrow aspirate suspension, and passing the bone marrow aspirate suspension through a porous, biocompatible, implantable substrate. Preferably, the substrate is sterile. Preferably, the method is performed intraoperatively using a bone marrow aspirate preferably from the graftee.

The present invention also provides a method for preparing an implantable graft having platelets on the surface thereof. The method comprises passing a suspension of platelets through a porous, biocompatible, implantable substrate. Suitable suspensions include, by way of example, bone marrow, isolated platelet concentrate, and blood which contains an anticoagulant.

Preparing a Bone Marrow Aspirate Suspension

Bone marrow aspirate contains plasma, nucleated connective tissue progenitor cells, nucleated hematopoietic cells, endothelial cells, and cells derived from contaminating peripheral blood, including red cells and platelets. Since bone marrow aspirate also contains peripheral blood, it is preferred that the bone marrow be collected in a syringe containing an anti-coagulant. Suitable anti-coagulants include, for example, heparin, sodium citrate, and EDTA. Preferably, the bone marrow aspirate is mixed with a sterile isotonic solution to provide a concentration in the range of from about 10 million to about 300 million nucleated cells/ml, preferably from about 20 million to about 250 million nucleated cells/ml, more preferably from about 50 million to about 200 million nucleated cells/ml. Suitable isotonic solutions include, for example, isotonic buffered salt solutions, such as Hank's Balanced Salt Solution and phosphate buffered saline, and tissue culture medium such as minimal essential medium. As used herein, the term "bone marrow aspirate suspension" refers to a bone marrow aspirate that has not been mixed with an isotonic solution and to a bone marrow aspirate that has been mixed with an isotonic solution.

Substrate

The substrate is made from a biocompatible, implantable graft material. Preferably, the material has a charged surface. Examples of biocompatible, implantable graft materials having a charged surface include ceramics comprising calcium phosphate such as, for example, hydroxyapatite or tri-calcium phosphate; as well as demineralized bone matrix; or mineralized bone matrix. Other suitable graft materials include biopolymers such as, for example, polylactic acid, polyglycolic acid, polygalactic acid, polycaprolactone, polyethylene oxide, polypropylene oxide, polysulfone, polyethylene, and polypropylene. Other suitable graft materials are hyaluronic acid, which may be purified with or without crosslinking, bioglass and collagen.

More preferably, cell adhesion molecules are bound to the surface of the substrate. The term "cell adhesion molecules" refers collectively to laminins, fibronectin, vitronectin, vascular cell adhesion molecules (V-CAM), intercellular adhesion molecules (I-CAM), tenascin, thrombospondin, osteonectin, osteopontin, bone sialoprotein, and collagens.

Optionally, the substrate has growth factors bound to the surface thereof. As used herein, the term "growth factors" encompasses any cellular product that modulates the growth or differentiation of other cells, particularly connective tissue progenitor cells. Growth factors include, but are not limited to, isoforms of platelet derived growth factors (PDGF), fibroblast growth factors, epithelial growth factors, isoforms of transforming growth factor Beta, insulin-like growth factors, and bone morphogenic proteins.

Optionally, the substrate has antibodies which have affinity for connective tissue progenitor stem cells bound to the surface thereof. Suitable antibodies, include by way of example, STRO-1, SH-2, SH-3, SH-4, SB-10, SB-20, and antibodies to alkaline phosphatase. Such antibodies are described in Haynesworth et al., Cell surface antigens on human marrow-derived mesenchymal cells are detected by monoclonal antibodies. *Bone* 13:69–80,1992a; Bruder, S. et al. Identification and characterization of a cell surface differentiation antigen on human osteoprogenitor cells. *Trans Ortho Res Soc* 21:574; 1996; Haynesworth, S. E., et al. Cell surface antigens on human marrow-derived mesenchymal cells are detected by monoclonal antibodies. *Bone* 13:69–80; 1992; Stewart, K., et al, Co-expression of the STRO-1 antigen and alkaline phosphatase in cultures of human bone and marrow cells. *J Bone Miner Res* 11(Suppl.):S142;1996; Flemming J E, et al., Monoclonal Antibody Against Adult Marrow-Derived Mesenchymal Stem Cells Recognizes Developing Vasculature in Embryonic Human Skin. *Developmental Dynamics* 212:119–132, 1998, and Bruder S P, et al, Monoclonal Antibodies Reactive With Human Osteogenic Cell Surface Antigens. *Bone* 21(3): 225–235, 1997.

Preferably, the substrate has a sufficient number of pores or passageways so that the total accessible surface area of the substrate is at least five times greater than a solid object having the same external dimensions. Thus, the preferred total surface area can be achieved by using a substrate which comprises a mass of powder, a mass of granules, a mass of fibers, or a highly porous block of substrate material. Preferably, the size of the pores in the substrate is greater that 20 $\mu$m, more preferably greater than 40 $\mu$m, most preferably greater than 100 $\mu$m.

Particularly suitable graft materials include, for example, isolated mineralized cancellous bone sections, powders or granules of mineralized bone, demineralized cancellous bone sections, powders or granules of demineralized bone, guanidine-HCl extracted demineralized bone matrix, sintered cortical or cancellous bone, coralline hydroxyapatite sold by Interpore under the trade name Interpore 500, or Interpore 200, and granular ceramics such as that incorporated into the bone graft substitute Collagraft sold by Zimmer, or filamentous sponges such as those made from collagen by Orquest.

Substrate Container

Preferably, the substrate is disposed in a container configured to retain the substrate in the container and to allow fluid and bone marrow cells to flow through the container. This is accomplished by using a container having two openings at either end thereof and comprising a member having one or more pores disposed between the substrate and one of the openings. Preferably, the pores of the member have a diameter of sufficient size to allow fluid and cells of the bone marrow aspirate suspension to flow therethrough and to retain the substrate in the container. Preferably, the length of the container is greater than the width of the container to increase residence time of the suspension in the substrate.

Preferably, the container is made of a material which is biocompatible and pyrogen-free. Suitable container materials include for example glass, plastic or metal. Although the container may comprise two fluid flow restrictors blocking the openings at either end of the container, preferably, a fluid flow regulator is attached to at least one end of the container to regulate flow of the bone marrow aspirate suspension through the substrate.

Conditions

To allow for implantation of the graft into a subject, it is preferred that the substrate be sterile and that the inner surface of the container which holds the substrate also be sterile. Preferably, the bone marrow aspirate suspension is permitted to flow through the sterile substrate under hydrostatic pressure which may be generated by external forces or by the force of gravity. Preferably, the linear elution rate of the suspension through the substrate is between 2 and 500 mm/minute, more preferably between 5 and 200 mm/minute, most preferably between 10 and 100 mm/minute.

Optionally, the effluent is collected sterilely in an effluent collector and recycled through the substrate one or more times to increase the number of connective tissue progenitor cells in the composite bone graft.

Optionally, a wash solution is passed through the substrate after the original bone marrow aspirate suspension and any effluents have been passed through the substrate. Preferably, the wash solution comprises a sterile, isotonic, buffered solution having a pH range of 7.3 to 7.5. Suitable wash solutions include, for example, phosphate-buffered saline, Hank's balanced salt solution, and minimal essential medium.

Optionally, growth factors or additional cells which secrete or present (i.e., express on their surface) growth factors are added to the composite bone graft prior to use, i.e, before, during or after the time the bone marrow aspirate suspension is passed through the substrate. Growth factors which may be added include for example, isoforms of platelet derived growth factors, fibroblast growth factors, epithelial growth factors, transforming growth factor Beta, insulin-like growth factor(s), parathyroid hormone (PTH) or PTH related peptide, and bone morphogenic proteins. Preferably, growth factors are added by passing a solution containing the growth factors through the substrate after all previous suspensions and solutions have been passed through the substrate. Alternatively, grow factors are added by incorporation into the wash solution. Platelets, which are known to secrete growth factors and to adhere to negatively charged surfaces, are added to the graft by passing a suspension of platelets, such as blood or platelet concentrate which contains an anti-coagulant, through the substrate.

The following examples of methods of preparing a composite bone graft are intended to illustrate but not to limit the present invention:

EXAMPLE 1

The present method for preparing a composite bone graft may be more readily understood by reference to FIG. 1 which depicts a preferred embodiment of the apparatus for performing the method. The apparatus, shown generally as 10, comprises a porous, biocompatible, implantable substrate 12, a container 14, for holding substrate 12, a reservoir 16 for holding the bone marrow aspirate suspension, a first fluid flow regulator 18, a second fluid flow regulator 20, and an effluent collector 22. Prior to preparation of the composite bone graft, all of the components of the apparatus are sterilized.

Following removal of top 23, the bone marrow aspirate suspension is introduced into reservoir 16. Then fluid flow regulator 18 is opened to allow the bone marrow aspirate suspension to flow out of reservoir 16 and into opening 30 in removable top 24 of container 14 and onto substrate 12.

As the suspension enters substrate 12, fluid flow regulator 20 which is attached to tip 34 of container 14 is opened to permit the bone marrow aspirate suspension to flow through porous member 32, through opening 36 of container 14 and into effluent collector 22.

Reservoir 16 and removable top 24 are then detached from container 14 and the improved composite bone marrow graft is then removed from container 14. The improved composite bone graft, which comprises substrate 12, an enriched population of connective tissue progenitor cells and a heterogenous population of other nucleated bone marrow cells, blood cells, and adherent growth factors and adhesion molecules derived from marrow and blood, is ready to use as an implant or in vitro.

EXAMPLE 2

Nine cylindrical disks of coralline hydroxyapatite (HA) measuring 13 mm in diameter and 5 mm in thickness were obtained from Interpore, Inc., Irvine, Calif. Each disk was placed in the tip of a vertically mounted 10 cc syringe barrel fitted with a stopcock. Marrow samples were taken from the anterior iliac crest of nine volunteer human subjects by aspiration. Samples were collected using a Lee-Lok bone marrow aspiration needle and a 10 cc syringe containing 1 ml of normal saline and 1000 units of Sodium-Heparin. Two ml of bone marrow were aspirated from each site. Marrow samples were suspended in α-MEM to prepare a suspension of marrow cells containing 50 million nucleated cells per ml. 2 ml of the marrow cell suspension were introduced in to the top of the syringe and the stopcock was adjusted to allow the marrow cell suspension to elute through the disk at 2 ml/minute. Each sample of effluent was recycled through the disk three times. After the effluent was collected, the disk was washed with 6 ml phosphate buffered saline at an elution rate of 2 ml/min, to remove loosely adherent cells.

The number of nucleated cells in the initial suspension, the effluents, and the washes were counted using a hemocytometer to determine the number of nucleated cells retained in the resulting composite bone grafts. To determine the number of connective tissue progenitors retained in the resulting composite bone grafts, the number of connective tissue progenitors in the initial suspensions, the effluent, and the washes were assayed by colony counting on tissue culture plastic. For colony counting, 500,000 nucleated cells from the original suspension, the effluents and the wash were plated in separate 35 mm diameter tissue culture wells and cultured in α-MEM containing dexamethasone ($10^{-8}$ M) and ascorbate (50 mg/ml) for 9 days. The cultured cells were then stained for alkaline phosphatase activity using N', N', dimethyl naphthol M—X phosphate as a substrate and Texas Fast Red as a stain. Alkaline phosphatase activity is a marker of osteoblastic differentiation. Thus, the number of colonies which stain positively for alkaline phosphatase activity reflect the number of connective tissue progenitors present in the original suspension, the effluents and the wash.

The number of nucleated cells and connective tissue progenitor cells which were retained on the substrate following each step were calculated by subtracting the number of nucleated cells and connective progenitor cells found in the effluents or wash from the number of nucleated cells and connective tissue progenitor cells in the initial suspension. The average number of nucleated cells and connective tissue progenitor cells retained in the nine composite bone grafts and the percentage of nucleated cells and connective tissue progenitor cells retained in the composite bone grafts are shown in Table 1.

EXAMPLE 3

Composite bone grafts were prepared as described in Example 2 except that bone marrow samples were taken from the anterior iliac crest of three different volunteer human subjects and the substrates used were cylindrical disks of demineralized human cancellous bone matrix obtained from Life Net, Virginia Beach, Va.

The number of nucleated cells and connective tissue progenitor cells retained in the composite grafts were determined as described above in Example 2. The average number of nucleated cells and connective tissue progenitor cells retained in the composite bone grafts and the percentage of nucleated cells and connective tissue progenitor cells retained in the composite bone grafts are shown in Table 1.

TABLE 1

Retention of Cells in Composite Bone Grafts made using disks of hydroxyapatite or demineralized human cancellous bone

|  | HA Disks | Cancellous Bone |
|---|---|---|
| Nucleated Cells in Original Suspension | $100 \times 10^6$ | $100 \times 10^6$ |
| Nucleated Cells Retained before Wash | $56.45 \times 10^6$ | $40.00 \times 10^6$ |
| Nucleated Cells Removed with Wash | $9.12 \times 10^6$ | $15.78 \times 10^6$ |
| Nucleated Cells Retained after Wash | $47.33 \times 10^6$ | $24.22 \times 10^6$ |
| CTPC in Original Suspension | 7800 | 11100 |
| CTPC Retained After Wash | 5162 | 4950 |
| Percent of all Nucleated Cells Retained | 47% | 24% |
| Percent of all CTPC Retained | 66% | 44% |
| Ratio of CTPC to Nucleated cells | 1.4 | 1.8 |
| Concentration of CTPC in Composite Bone Graft vs Concentration of CTPC in Original Suspension | 2.8 | 1.3 |

CTPC = Connective Tissue Progenitor Cells

As shown in Table 1, composite grafts made with a substrate of hydroxyapatite or demineralized human cancellous bone retained a significant percentage of the nucleated cells (47% and 24%, respectively) and an even greater percentage of the connective tissue progenitor cells (66% and 44%, respectively) in the original suspension. As also shown in Table 1, washing substrates of cancellous bone or coralline hydroxyapatite resulted in removal of a mean of 16.2% (range 10%–33%) of the nucleated cells which are initially retained in a coralline HA substrates and 39.45% (range 33–86%) of the cells retained in a demineralized cancellous bone matrix substrates.

As shown in Table 1, the composite grafts made with either the hydroxyapatite or the demineralized human cancellous bones selectively retained the connective tissue progenitor cells as compared to other marrow derived nucleated cells. This selective retention is illustrated by the ratio (>1) of % connective tissue progenitor cells retained vs % nucleated cells retained on the substrate. Thus, the composite bone grafts prepared with either the hydroxyapatite disks or the demineralized human cancellous bone disks comprise an enriched population of connective progenitor cells.

Concentration of connective tissue progenitor cells above that found in the original bone marrow sample is illustrated by dividing the number of connective tissue progenitor cells retained by the volume of the disks (0.63 cm$^3$). As shown in Table 1, the mean concentration of connective tissue progenitor cells retained in the composite bone grafts comprising HA disks was 2.8 times greater than the concentration in the original marrow sample. Similarly, the mean concentration of connective tissue progenitor cells retained in the composite bone grafts comprising demineralized cancellous bone matrix was 1.3 times greater than in the original marrow sample.

EXAMPLE 4

Forty-five composite bone grafts were prepared as described in Example 2 except that the concentration of nucleated cells in the marrow suspension was varied between 5, 10, 20, 40, and 50 million cells/ml from each of the nine human donors. The number of nucleated cells and connective tissue progenitor cells retained on each of the resulting composite bone grafts were determined as described in Example 2. The results are shown in FIGS. 2a and 2b.

Figure 2A:
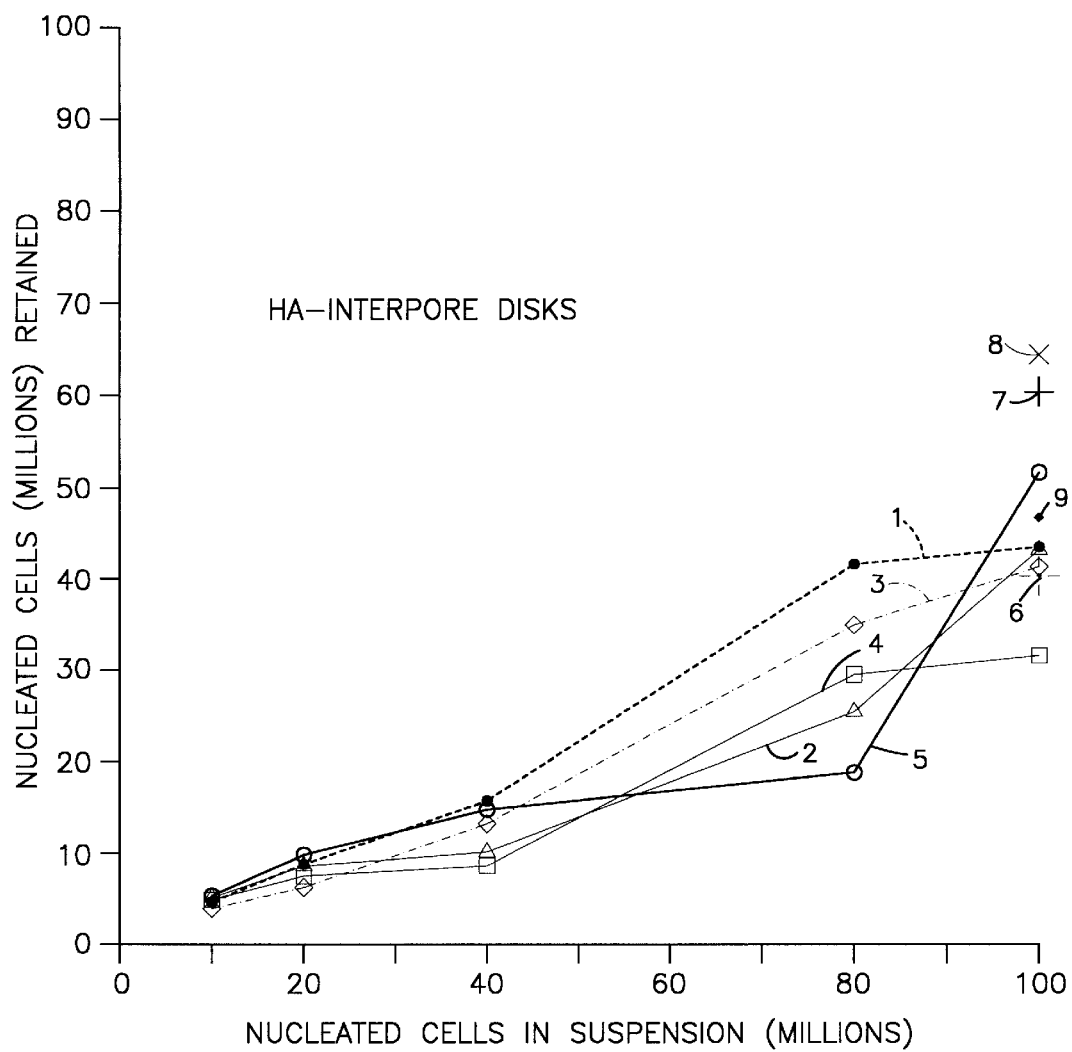
FIG. 2a is a graph showing the effect of increasing the concentration of nucleated cells in the bone marrow aspirate suspension on the number of nucleated cells retained on a composite bone graft comprising a hydroxyapatite substrate. Data summarizes results from nine human subjects using identical conditions.
Figure 2B:
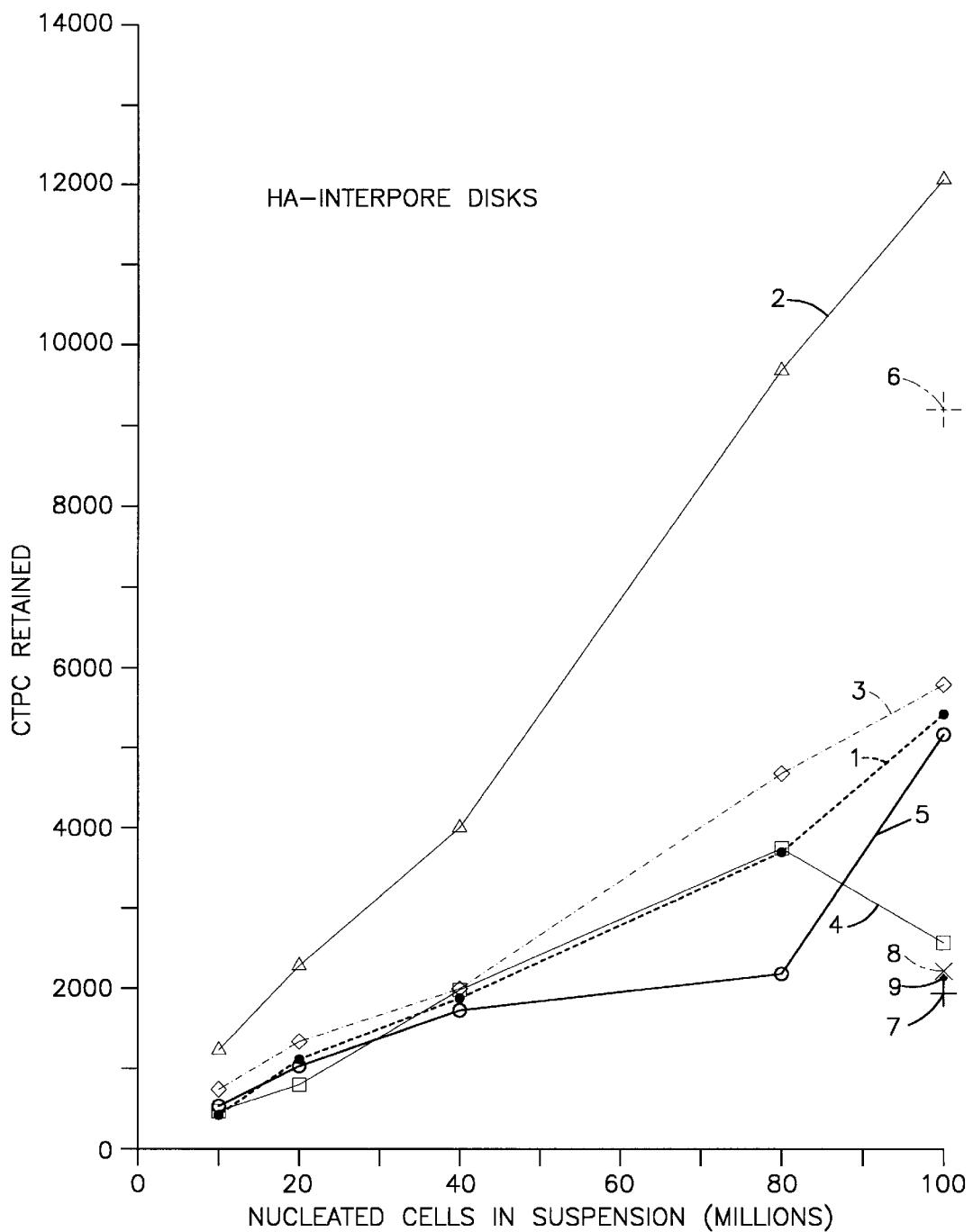
FIG. 2b is a graph showing the effect of increasing the concentration of nucleated cells in the bone marrow aspirate suspension on the number of connective tissue progenitor cells retained on a composite bone graft comprising a hydroxyapatite substrate. Data summarizes results from nine human subjects using identical conditions.

As shown in FIGS. 2a and b, the number of nucleated cells and the number of connective tissue progenitor cells retained in the composite bone grafts increased in an essentially linear fashion as the number of marrow cells passed through the hydroxyapatite substrate was increased, indicating that saturation of the hydroxyapatite substrate with marrow derived cells did not occur over the range of cells to substrate volume evaluated.

EXAMPLE 5

Fifteen composite bone grafts were prepared using disks of demineralized cancellous bone matrix as described in Example 2 except that the concentration of nucleated cells in the marrow suspension was varied between 5, 10, 20, 40, and 50 million cells/ml from each of the three human donors. Data reflecting the number of nucleated cells and the number of connective tissue progenitor colonies retained in the resulting composite bone grafts is presented in FIG. 3a and 3b.

Figure 3A:
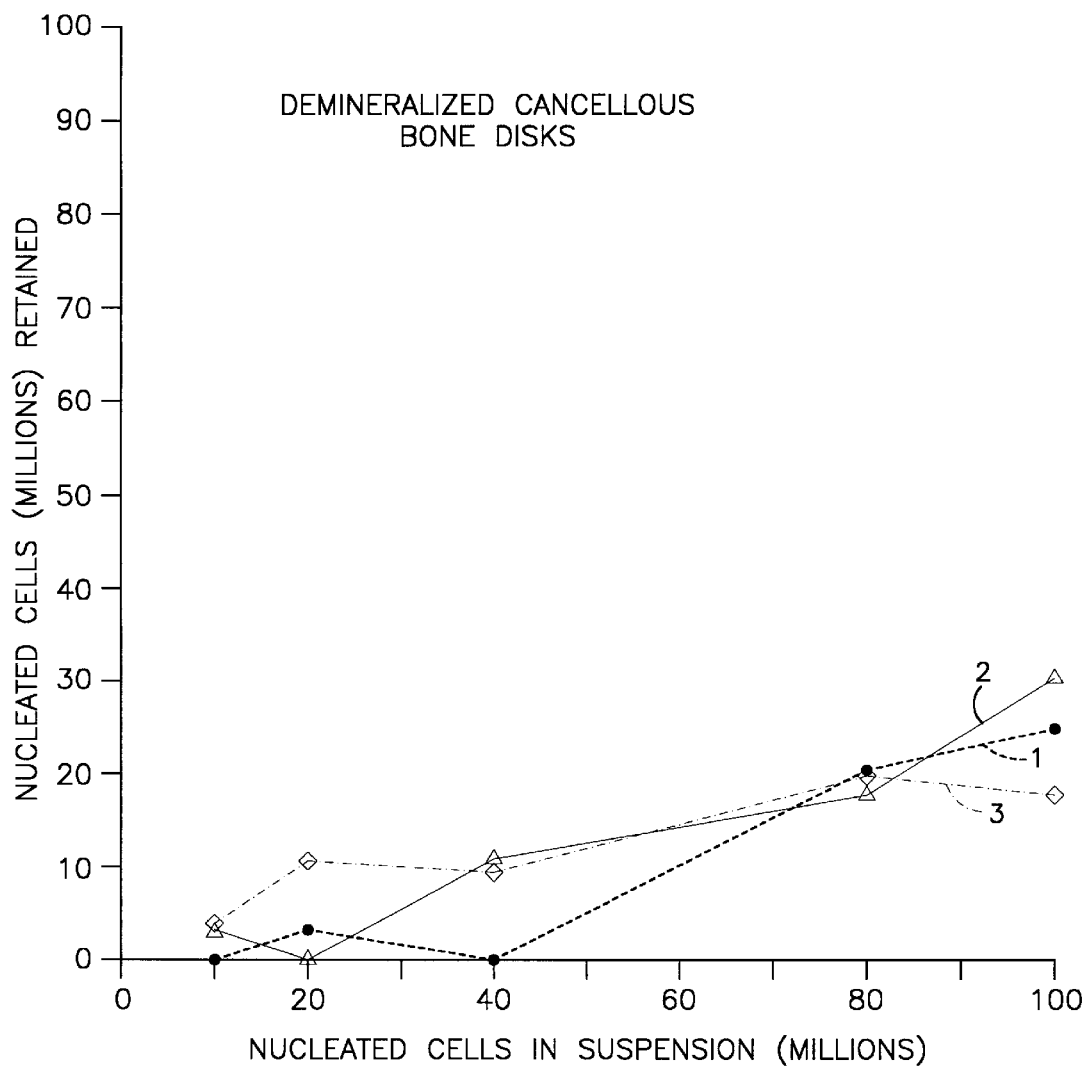
FIG. 3a is a graph showing the effect of increasing the concentration of nucleated cells in the bone marrow aspirate suspension on the concentration of nucleated cells retained on a composite bone graft comprising a demineralized human cancellous bone matrix substrate.
Figure 3B:
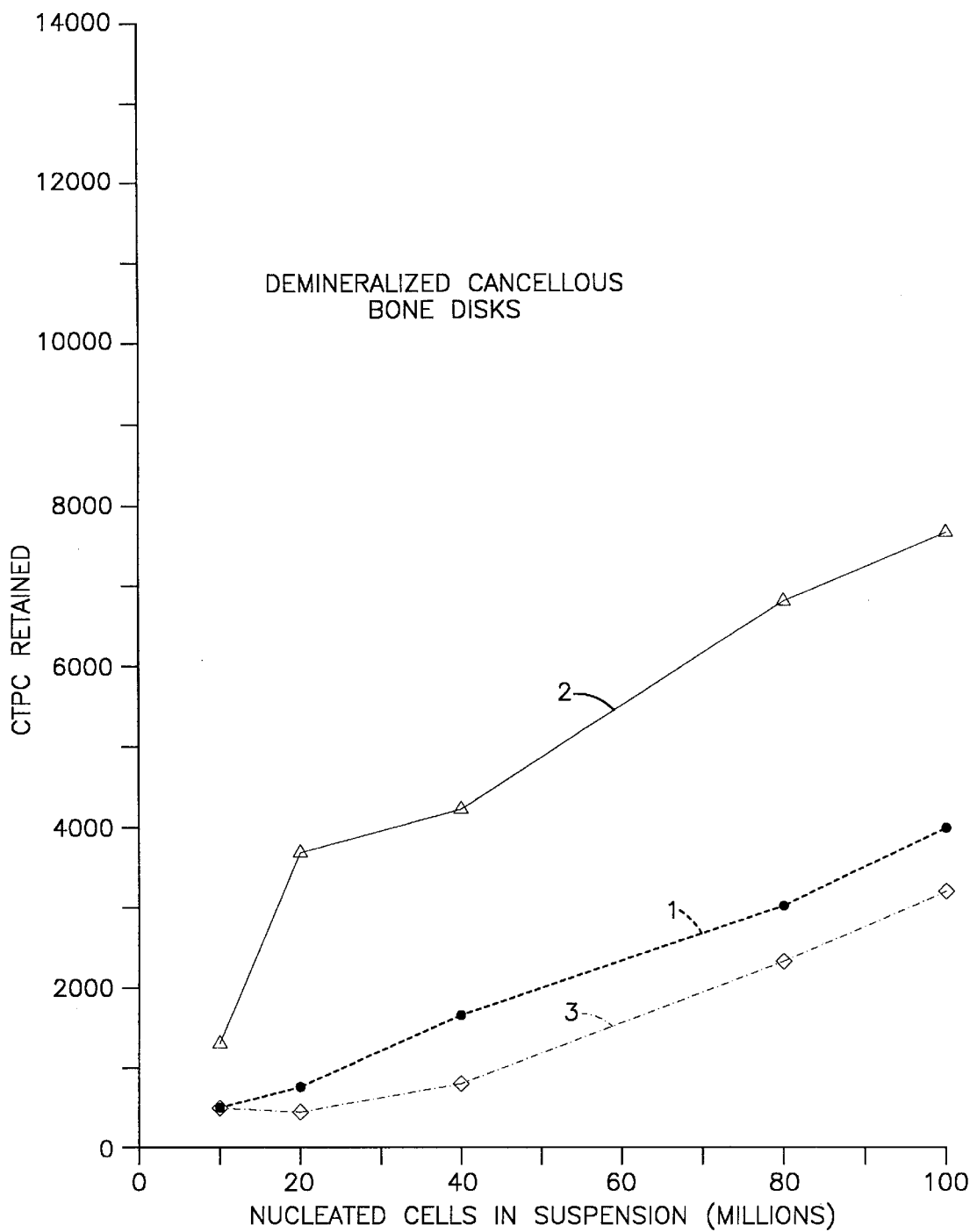
FIG. 3b is a graph showing the effect of increasing the concentration of nucleated cells in the bone marrow aspirate suspension on the number of connective progenitor cells retained on a composite bone graft comprising a demineralized human cancellous bone matrix substrate. Data summarizes results from three human subjects using identical conditions.

As shown in FIGS. 3a and 3b, the number of nucleated cells and the number of connective tissue progenitor cells retained in the composite bone grafts increased in an essentially linear fashion as the number of marrow cells passed through the demineralized cancellous bone matrix substrate increased, indicating that saturation of the substrate with marrow derived cells did not occur over the range cells to substrate volume evaluated.

EXAMPLE 6

A composite bone graft was prepared as described in Example 2 using a 2 cc marrow suspension containing 5 million nucleated cells/ml except that the substrate was not washed with 6 ml of phosphate buffered saline after loading. Compared to an identical disk loaded in an identical manner which was washed as in Example 2, the unwashed disk retained the same number of connective tissue progenitors (1000 in the case shown) and a greater number of marrow derived nucleated cells (2.2 million vs 1.2 million in the washed example). After culture for 24 days in vitro, the presence of these additional cells resulted in greater proliferation and differentiation of the connective tissue progenitors. This was manifest by a greater surface area covered by cells that expressed alkaline phosphatase activity, which is a marker of osteoblastic differentiation.

EXAMPLE 7

A composite bone graft was prepared as in Example 2 except that the bone marrow suspension was recycled over the hydroxyapatite disk only once, rather than three times. This reduced the number of cells and connective tissue progenitors which remained attached to the disk of coralline hydroxyapatite.

EXAMPLE 8

Three composite bone grafts were prepared as in Example 2 except that the concentration of nucleated cells in the marrow suspension was increased from 100 to 150 million nucleated cells per ml. This increase in the number of cells passed through the hydroxyapatite disks increased the number of nucleated cells and connective tissue progenitor cells retained in the composite bone grafts by a mean of 66.84% and 52.0%, respectively. These highly cellular suspensions exhibited increased viscosity and slower elution flow rates.

EXAMPLE 9

Heparinized human bone marrow samples were harvested with informed consent during elective Orthopaedic procedures by repeated aspiration of 2 cc samples from separate sites along the anterior iliac crest. Sterile samples of human allograft bone matrix powder (425–850 m dia, 0.1 ml volume) (Musculoskeletal Transplant Foundation, USA) were loaded into 1 ml syringes. A screen retained the particles in the syringe. Samples of bone marrow cell suspensions were passed through the allograft powder at defined concentrations and flow rates. Samples of marrow were assayed for cell number and CFU-Os using established techniques before and after passage through the matrix. The number of cells and CFU-Os retained in the matrix were calculated. A selection ratio for CFU-Os vs nucleated cells was also calculated (CFU-Os retained/CFU-Os loaded, cells retained/cells loaded). A selection ratio greater than 1.0 indicating that CFU-Os were positively selected over other marrow derived nucleated cells.

The results indicated that cell and CFU-O retention on demineralized allograft powder increased as the number of cells loaded increased from 25 million cells to 200 million cells, where saturation occurred (flow rate 30 mm/min). Saturated matrices retained a mean of $80 \times 10^6$ nucleated cells (range 20 to $140 \times 10^6$) and 3800 CFU-Os (range 500 to 6600). This mean concentration of CFU-Os of 38,000 / ml was 19 fold greater that the mean concentration of CFU-Os in the original aspirate. The mean selection ratio at a loading density of 25 million cells was 2.4, but fell to 1.4 at a loading density of 200 million cells, indicating that CFU-Os appear to bind selectively to the matrix surface, but once the matrix surface is saturated with cells, further accumulation of cells in the matrix void spaces is much less selective. Comparison of flow rates from 15 mm/min to 60 mm/min revealed no influence of flow rate in this range on the number of cells or CFU-Os retained. Recycling samples through the matrix up to three times did not increase the retention of cells or CFU-Os. As shown in this example, human bone marrow derived osteoblastic progenitors harvested by aspiration can be concentrated in allograft matrix 19 fold by use of a rapid method suitable for intra-operative use.

These methods of preparing composite bone marrow grafts typically required less than sixty minutes to complete. Thus, these methods can be performed while the bone marrow donor/graftee is in the operating room. Accordingly, the number of occasions the graftee must undergo invasive procedures to receive a composite bone graft can be reduced by using these methods.

The improved composite bone grafts prepared according to these methods comprised a biocompatible, implantable substrate and an enriched population of connective tissue progenitor cells. As used herein the term "enriched population of connective tissue progenitor cells" means that the percentage of connective tissue progenitor cells as compared to all nucleated bone marrow cells is greater in the composite bone marrow graft than in the original bone marrow aspirate. In addition, the concentration of the connective tissue progenitor cells in the improved composite bone marrow grafts was about two times greater than the concentration of these cells in the original aspirate.

The improved composite bone grafts also comprised a population of nucleated cells other than connective tissue progenitor cells, including endothelial cells and hematopoietic cells derived from bone marrow, and a population of platelets derived from peripheral blood. The red blood cells and liquid plasma in the bone marrow aspirate suspension are not selectively retained in the composite bone grafts and, thus, the improved composite bone grafts typically contain less than five % of the red blood cells in the original suspension. Proteins and adhesion molecules present in plasma are also concentrated on the surface of the substrate as a combined function of their concentration in the plasma and relative affinity for the substrate surface.

The improved composite bone graft is suitable for implantation into the bone marrow aspirate donor or into an immunologically compatible host. The improved composite bone graft is also useful for assessing the effect of exogenous cytokines, hormones and other bioactive molecules on the proliferation and differentiation of connective tissue progenitor cells in vitro.

While the method for preparing an implantable graft has been described to some degree of particularity, various adaptations and modifications can be made without departing from the scope of the invention as defined in the appended claims.

What is claimed is:

1. A kit for preparing a composite bone graft from a bone marrow aspirate suspension comprising:
   (a) a porous, biocompatible, implantable substrate; and
   (b) a container for holding said substrate, said container configured to retain said substrate and to permit flow of the bone marrow aspirate suspension therethrough, said container having an inner surface and two ends, each of said ends defining an opening.

2. The kit of claim 1 wherein said substrate is sterile.

3. The kit of claim 1 further comprising
a fluid flow regulator attachable to one end of said container for regulating the rate of flow of the bone marrow aspirate suspension through said substrate.

4. The kit of claim 2 further comprising
(a) a reservoir for holding the bone marrow aspirate suspension; and
(b) a fluid flow regulator attachable to said reservoir for regulating flow of the bone marrow aspirate suspension from said reservoir into said container.

5. The kit of claim 2 further comprising an effluent receiver for receiving an effluent of the bone marrow aspirate suspension from said container.

6. The kit of claim 2 wherein said substrate has external dimensions and a total accessible surface area at least five times greater than the surface area of a solid object having the same external dimensions.

7. The kit of claim 2 wherein said substrate is formed from a ceramic comprising calcium phosphate or bioglass.

8. The kit of claim 1 wherein said substrate is formed from a material selected from the group consisting of collagen, mineralized bone, and demineralized bone.

9. The kit of claim 1 wherein said substrate is formed from hyaluronic acid or a synthetic biopolymer.

10. The kit of claim 2 wherein said substrate comprises cell adhesion molecules bound to the surface thereof.

11. The kit of claim 2 wherein said substrate comprises growth factors bound to the surface thereof.

12. The kit of claim 1 wherein said substrate comprises antibodies that bind to surface antigens expressed on the surface of connective tissue progenitor cells or platelets, wherein said antibodies are bound to the accessible surface of said substrate.

13. The kit of claim 1 wherein said substrate has pores or passageways having a diameter greater than $40\mu$.

14. The kit of claim 2 wherein the container further comprises a porous member for retaining the substrate within the container.

15. The kit of claim 1 wherein the container is made of a material that is bio compatible.

16. A kit for preparing an implantable graft having platelets attached to the surface thereof, comprising:
(a) a sterile, porous, biocompatible, implantable substrate, said substrate having pores or passageways having a diameter of greater than 40 $\mu$m; and
(b) a container for holding said substrate, said container configured to retain said substrate and to permit flow of a platelet suspension therethrough, said container having an inner surface and two ends, each of said ends defining an opening.

17. The kit of claim 16 wherein said substrate is formed from a synthetic biopolymer.

18. The kit of claim 16 wherein said substrate is formed from hyaluronic acid.

19. The kit of claim 16 wherein said substrate has external dimensions and a total accessible surface area at least five times greater than the surface area of a solid object having the same external dimensions.

20. A composite bone marrow graft comprising:
(a) a porous, biocompatible, implantable substrate;
(b) a heterogenous population of nucleated bone marrow cells; and
(c) an enriched population of connective tissue progenitor cells.

* * * * *